US012144917B2

(12) United States Patent
Pollari et al.

(10) Patent No.: US 12,144,917 B2
(45) Date of Patent: Nov. 19, 2024

(54) ARTERIAL CANNULA

(71) Applicants: Francesco Pollari, Nuremberg (DE); Michela Cuomo, Nuremberg (DE)

(72) Inventors: Francesco Pollari, Nuremberg (DE); Michela Cuomo, Nuremberg (DE)

( * ) Notice: Subject to any disclaimer, the term of this patent is extended or adjusted under 35 U.S.C. 154(b) by 745 days.

(21) Appl. No.: 17/430,232

(22) PCT Filed: Feb. 15, 2019

(86) PCT No.: PCT/EP2019/053763
§ 371 (c)(1),
(2) Date: Aug. 11, 2021

(87) PCT Pub. No.: WO2020/164727
PCT Pub. Date: Aug. 20, 2020

(65) Prior Publication Data
US 2022/0160945 A1    May 26, 2022

(51) Int. Cl.
*A61M 1/36* (2006.01)
*A61M 60/113* (2021.01)
(Continued)

(52) U.S. Cl.
CPC ........ *A61M 1/3659* (2014.02); *A61M 1/3666* (2013.01); *A61M 60/113* (2021.01);
(Continued)

(58) Field of Classification Search
CPC .. A61M 1/3659; A61M 60/247; A61M 60/38; A61M 60/865; A61M 60/113; A61M 60/857; A61M 1/3666
See application file for complete search history.

(56) References Cited

U.S. PATENT DOCUMENTS 4,173,981 A * 11/1979 Mortensen ........ A61M 25/0021
604/8
5,584,803 A * 12/1996 Stevens ................ A61F 2/2433
604/6.16
(Continued)

FOREIGN PATENT DOCUMENTS

DE    699 11 950 T2    7/2004
EP    1 990 067 A2    11/2008
(Continued)

OTHER PUBLICATIONS

International Search Report and Written Opinion of the International Searching Authority for International Patent Application No. PCT/EP2019/053763 mailed Oct. 29, 2019, 12 pages.

*Primary Examiner* — Guy K Townsend
(74) *Attorney, Agent, or Firm* — Merchant & Gould P.C.

(57) ABSTRACT

An arterial cannula connects to a heart-lung machine for supplying a patient with oxygen-rich blood and includes a tubular body having a front end region for positioning at the aortic arch, a main region, and a rear end region for connection to the supply side. The length of the tubular body is dimensioned so that the cannula can be placed at the femoral artery and extends to the aortic arch. The tubular body is flexible and includes a lumen, and perforations in the front end region. The front end region is pre-curved, following the shape of the aortic arch. An insertion aid is located inside the tubular body for placing the cannula and is slidable into or withdrawable from the tubular body after the cannula has been placed. The curvature of the front end region adjusts automatically after the cannula is placed and the insertion aid withdrawn.

18 Claims, 7 Drawing Sheets

(51) Int. Cl.
*A61M 60/247* (2021.01)
*A61M 60/38* (2021.01)
*A61M 60/857* (2021.01)
*A61M 60/865* (2021.01)

(52) U.S. Cl.
CPC .......... *A61M 60/247* (2021.01); *A61M 60/38* (2021.01); *A61M 60/857* (2021.01); *A61M 60/865* (2021.01)

(56) References Cited

U.S. PATENT DOCUMENTS

| | | | | |
|---|---|---|---|---|
| 5,702,368 A * | 12/1997 | Stevens | ............ | A61M 25/0152 604/4.01 |
| 5,766,151 A * | 6/1998 | Valley | ............ | A61M 39/0247 604/103.07 |
| 5,769,812 A * | 6/1998 | Stevens | ............ | A61M 25/0662 604/509 |
| 5,792,094 A * | 8/1998 | Stevens | ............ | A61F 2/2433 604/509 |
| 5,795,325 A * | 8/1998 | Valley | ............ | A61M 25/0662 604/509 |
| 5,814,016 A * | 9/1998 | Valley | ............ | A61M 25/1002 604/96.01 |
| 5,868,702 A * | 2/1999 | Stevens | ............ | A61M 25/0041 604/6.14 |
| 5,885,238 A * | 3/1999 | Stevens | ............ | A61B 17/29 604/6.14 |
| 5,916,193 A * | 6/1999 | Stevens | ............ | A61M 1/3653 604/509 |
| 6,139,517 A * | 10/2000 | Macoviak | ............ | A61M 25/1002 604/8 |
| 6,251,093 B1 * | 6/2001 | Valley | ............ | A61M 1/3659 604/99.01 |
| 6,254,563 B1 * | 7/2001 | Macoviak | ............ | A61M 25/1011 604/99.04 |
| 6,508,777 B1 * | 1/2003 | Macoviak | ............ | A61M 25/1011 604/9 |
| 6,579,259 B2 * | 6/2003 | Stevens | ............ | A61M 25/0662 604/96.01 |
| 6,695,864 B2 * | 2/2004 | Macoviak | ............ | A61M 25/1011 606/200 |
| 6,702,773 B1 * | 3/2004 | Macoviak | ............ | A61M 1/3613 604/4.01 |
| 6,913,600 B2 * | 7/2005 | Valley | ............ | A61B 17/00234 604/509 |
| 2001/0044591 A1 * | 11/2001 | Stevens | ............ | A61M 25/0662 604/6.14 |
| 2002/0010411 A1 * | 1/2002 | Macoviak | ............ | A61M 25/1002 604/8 |
| 2002/0016566 A1 * | 2/2002 | Bertolero | ............ | A61B 90/36 604/102.03 |
| 2004/0162519 A1 * | 8/2004 | Helkowski | ............ | A61M 1/3659 604/103.09 |
| 2005/0113631 A1 * | 5/2005 | Bolling | ............ | A61M 25/003 600/16 |
| 2022/0160945 A1 * | 5/2022 | Pollari | ............ | A61M 60/38 |

FOREIGN PATENT DOCUMENTS

WO 97/37716 A1 10/1997
WO 2006/019714 A1 2/2006

* cited by examiner

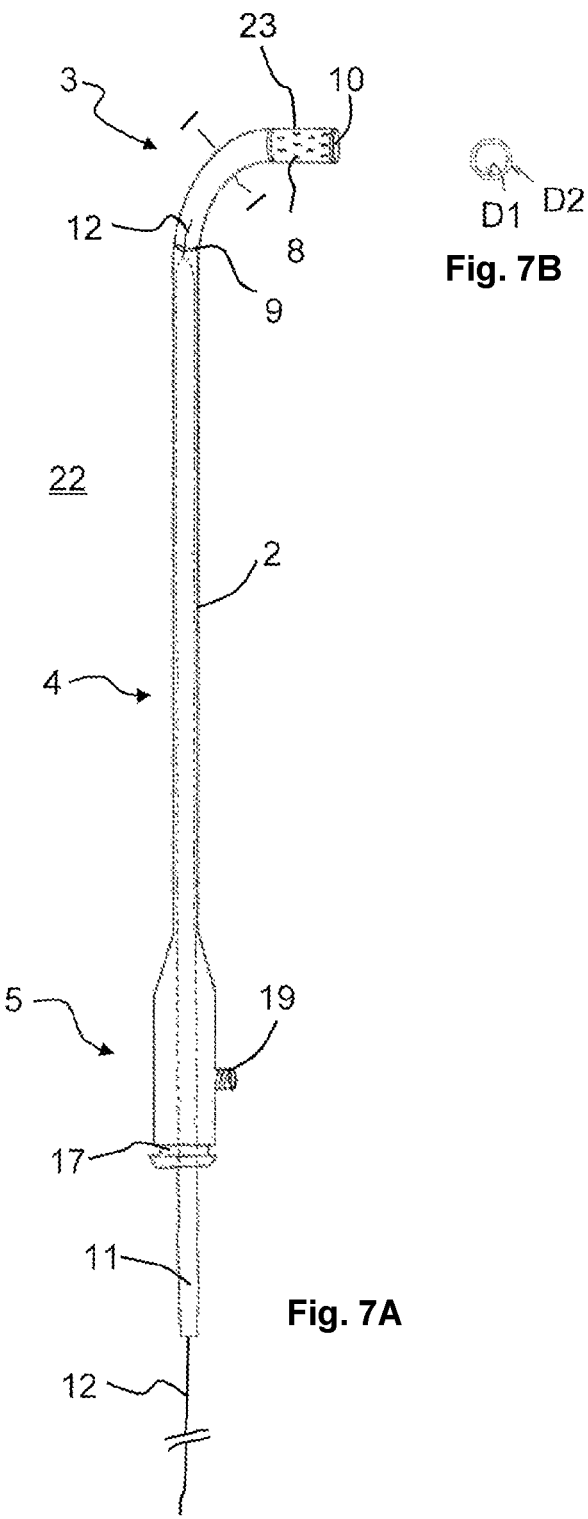

ARTERIAL CANNULA

This application is a National Stage Application of PCT/EP2019/053763, filed 15 Feb. 2019, and which application is incorporated herein by reference. To the extent appropriate, a claim of priority is made to the above-disclosed application.

The present invention relates to an arterial cannula to be connected to a heart-lung machine or to a Mechanical Circulatory Support System (MCS) to ensure a circulation of blood for the entire body, for example, in the event of a minimally invasive heart operation, high-risk percutaneous coronary interventions, in the event of heart stoppage or a low cardiac output syndrome.

TECHNOLOGICAL BACKGROUND

A cardiovascular bypass system, also known colloquially as a heart-lung machine, is used to temporarily replace the functions of the heart and lungs by supplying a flow of oxygen-rich blood to the patient's circulatory system. In this process, de-oxygenated blood is diverted from the patient's venous system, pumped through a blood oxygenator and the oxygen-rich blood is then fed back into the patient's arterial system in order to allow arterial perfusion of the body.

In order to achieve a central perfusion of the body with oxygen-rich blood in the forward flow (flow from the ascending aorta to the descending aorta), a relatively short cannula has heretofore been placed directly on the ascending aorta or aortic arch. This method is called "central cannulation." A central cannulation requires a sternotomy (longitudinal transection of the sternum) and surgery on the open chest.

However, there is already a method in which oxygen-rich blood is delivered to the aorta via a peripheral cannula. The cannula is inserted through the femoral artery. In this case, the blood flow is inverted because the oxygen-rich blood has to flow back from a peripheral vessel (e.g. the femoral artery) to the aorta in order to reach the vital organs such as the brain, kidneys, lungs and the digestive organs. This is a minimally invasive procedure, which only requires inserting the cannula into the femoral artery. Sternotomy and open-chest surgery can be avoided. However, there is a higher risk of cerebral damage by an embolism, mobilized in the descending aorta by the inverted blood flow there. In addition, if there is residual heart activity, the supra-aortic blood vessels receive more de-oxygenated blood from the heart in the forward flow than oxygen-rich blood via the heart-lung machine because of the inverted blood flow.

As a result, there is a certain tension between the requirement of an intervention that is as patient-friendly as possible on the one hand and the exclusion of complications on the other.

DOCUMENTED PRIOR ART

An arterial cannula according to the preamble of claim 1 is known from U.S. Pat. No. 4,173,981. This is an arterial cannula to be inserted in the pelvic region which requires surgical cut (incision) in the femoral artery and is inserted therein without an insertion aid. The cannula is straight and has a shape that tapers toward the front end. Furthermore, it has a maximum of two circular perforations, arranged on one side of the cannula, at certain points along the cannula, at which oxygen-rich blood can escape from the cannula. The openings are in locations of arteries branching off the main artery (such as supra-aortic branches, renal artery, and iliac artery). In addition to the tapering shape, the material of the cannula must be resilient on the one hand, and flexible on the other, in order to allow the cannula to be inserted and maneuvered within the aorta.

A circulatory support system having an artery cannula insertion subsystem is known from DE 699 11 950 T2 in which an occlusion balloon is provided in the front end region of the cannula after a plurality of individual perforations are individually applied on one side of the cannula. The balloon is inflated after the cannula is placed through an additional channel arranged on the side of the wall in the cannula. A guide wire can be used for placing the cannula. Due to the sealing by the balloon, no oxygen-rich blood can get through the openings to the side downstream from the balloon. It results from this that the aortic arch is not supplied with oxygen-enriched blood directly in the region of cardiac outlet. There is also the risk that the balloon can accidentally occlude a blood vessel (e.g. a cerebral vessel).

Problem Addressed by the Present Invention

The object of the present invention is to provide an arterial cannula with which a good supply of oxygen-enriched blood is made possible while reducing the susceptibility to complications.

Solution of the Problem

The present object is achieved by the features of claim 1. Expedient embodiments of the invention are claimed in the dependent claims.

Because the front end region of the tubular body is (completely or at least partially) pre-curved, an insertion aid is provided which is located inside the tubular body for placing the cannula and can be slid into the tubular body or withdrawn therefrom after the cannula has been placed, such that the curvature of the front end region of the tubular body adjusts automatically after the cannula has been inserted and the insertion aid is withdrawn, the result is that the front region of the cannula is optimally positioned in the aortic arch on the one hand, and on the other hand the cannula can be inserted in a particularly gentle way over the relatively long distance from the femoral artery through the aorta to the aortic arch. The risk of plaque detachment during placement or insertion of the cannula is significantly reduced. Furthermore, a tubular body with a substantially constant diameter or lumen, at least as far as its front end region and main region are concerned, can be used. This in turn results in a sufficient volume of oxygen-rich blood being transported to the aortic arch under lower pressure compared to a known cannula with a diameter that diminishes in the forward direction, and the entire aortic arch can thus be adequately supplied. The cannula is applied by a percutaneous technique. By puncturing the femoral artery, a wire is advanced through the femoral artery to the aortic arch. The cannula together with the insertion aid (or mandrel) can then be pushed onto the wire up to the position in the aortic arch. This percutaneous method is known as the "Seldinger Technique" and is used to insert catheters and other devices into the body without surgical incisions. The cannula according to the invention thus enables a supply of oxygen-rich blood as was previously possible with the central cannulation, but without the necessary surgical intervention and specifically neither directly on the aortic arch nor on the femoral artery.

Because perforations are only provided in the front end region of the tubular body, that is, in contrast to the prior art, and not in its main region as well, the risk of complications is reduced. This is because perforations provided in the main region create the risk that the cannula will not be recognized during use if perforations are closed in the front region of the tubular body (possibly due to a position of the cannula with wall contact). This is because there is no noticeable increase in pressure on the pressure measuring device, because oxygen-rich blood, as before, can still escape through the perforations positioned in the main part.

The tubular body expediently has a single lumen. On the one hand, this results in no stiffening of the tubular body in a preferred orientation, which in turn would make it more difficult to insert the cannula, and on the other hand, the cannula is also very easy to manufacture technically.

According to an expedient embodiment of the cannula according to the invention, the lumen is circular.

The lumen and/or the tubular body expediently have an at least substantially constant diameter D1 or D2 in the longitudinal direction of the cannula in the front end region and/or in the main region.

Because the front end region of the tubular body cannot be expanded and/or inflated, oxygen-enriched blood can reach the cardiac outlet via the cannula. Moreover, no additional channels have to be provided for the supply of compressed gas to expand the cannula.

According to an expedient embodiment, at least six, particularly preferably at least twelve, perforations are arranged on the front end region of the cannula or the tubular body. This ensures that a sufficient amount of oxygen-rich blood is supplied while avoiding excessive pressure in the aortic arch.

Because the perforations are arranged, preferably symmetrically, around the circumference of the tubular body, a sufficient supply of oxygen-rich blood is ensured even if some perforations do not allow sufficient escape of oxygen-rich blood due to wall contact.

Because the perforations have a shape with a preferred orientation, in particular an elongated and/or oval shape, an improved exit of oxygen-rich blood in the direction of flow along the wall of the tubular body is achieved.

Because the preferred orientation of the shape of the perforations extends in the longitudinal direction of the tubular body, it can be avoided that the tip of the insertion aid is accidentally caught in a perforation and/or may even move outward through a perforation under certain circumstances.

Alternatively, the perforations can also have a round diameter.

The fact that the perforations have a hole diameter D3 or hole width which increases from the inside to the outside of the tubular body, preferably continuously, reduces the risk of the outer edges of the tubular body in the region of the perforations detaching plaque deposits within the aorta when the cannula or the front end region of the tubular body is inserted.

It is particularly useful if the perforations on the outside of the tubular body are rounded, that is, are rounded from the outer wall to the inner wall of the tubular body, so that the perforations open in a round course from the inner wall to the outer wall, that is, they widen continuously.

To monitor the insertion of the tubular body, markers, in particular so-called contrast medium markers (for example, in the form of radiopaque material), are provided, expediently at the front end region thereof.

Because the markers define the region of the perforations and/or the region of curvature, the exact position of the respective region can be monitored during the insertion of the cannula. A marker is expediently located at the distal end of the tubular body. Another marker is at the beginning of the section that contains the perforations.

According to a further embodiment, the front end region of the cannula can have an, at least substantially, straight section at its distal end, in which the perforations are located, preferably exclusively. The pre-curved region of the front end region of the cannula can be designed without perforations. This can bring additional handling advantages.

The insertion aid expediently has a mandrel (or straightener or extensor), which can be pushed into the tubular body and/or pushed through it, so that the cannula at the beginning of the insertion of the same into the femoral artery and also during the introduction from the femoral artery through the aorta is extended up to the aortic arch surmounting the pre-curvature of the front part of the tubular body. In addition to the extension of the pre-curvature of the cannula, the insertion aid or the mandrel also serves to ensure the necessary rigidity in order to advance the cannula (without it bending). The tubular body and the mandrel can be moved independently of one another by the doctor performing the procedure. The mandrel preferably has a rounding at its distal end and/or a gradual cross-sectional tapering toward the distal end.

The insertion aid comprises an extremely flexible wire which can be slid into the tubular body and/or pushed through it and by means of which the direction of the front end region of the tubular body, preferably the tubular body and the mandrel, can also be influenced by the curvature of the wire due to arterial wall contact during placement of the cannula. The wire is provided so that the cannula and the insertion aid or the mandrel can be advanced in the direction determined by the wire. For this purpose, the insertion aid or the mandrel comprises a channel in which the wire runs.

Both the mandrel and the wire are removed after the cannula is inserted.

According to a further embodiment, the cannula can be equipped, preferably in its rear end region, with a branch and a tap. This allows the system to be vented and/or flushed as needed or be connected to a pressure measuring device.

DESCRIPTION OF THE INVENTION USING EMBODIMENTS

In the following, expedient embodiments of the present invention are described in detail in reference to figures of the drawing. In the drawings.

Figure 1:
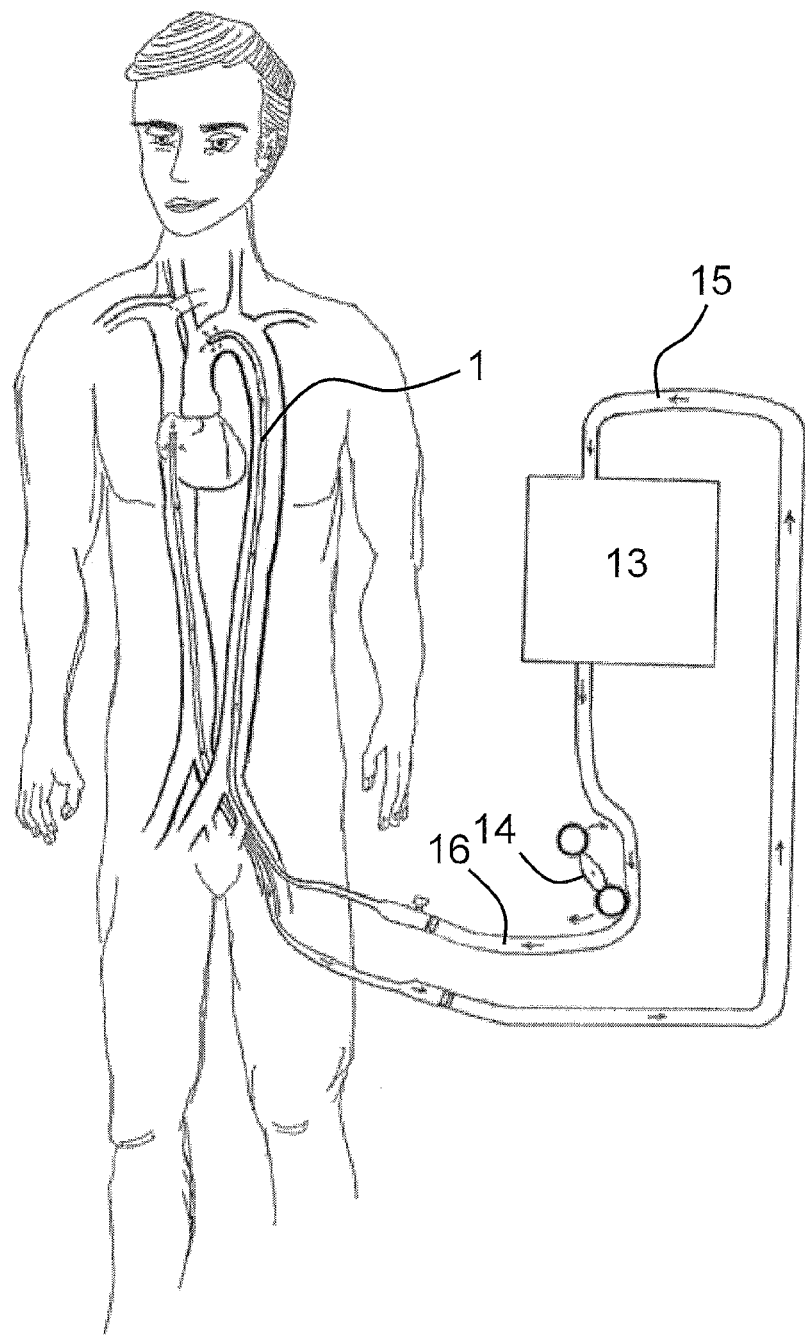
FIG. 1 is an overview of the embodiment of an arterial cannula according to the invention in the inserted state.
Figure 6:
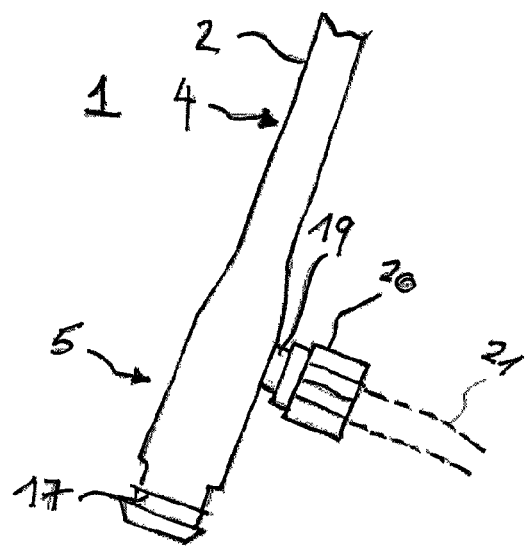
Figure 5A:
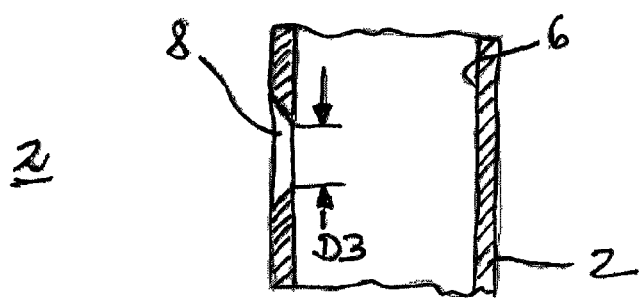
Figure 5B:
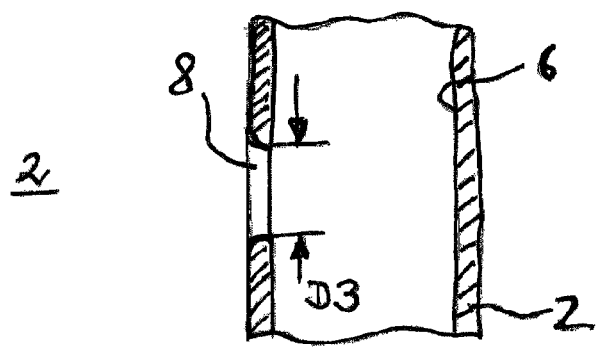

FIG. 5 a sectional view of the front part of the tubular body with a first embodiment of the shape of the perforations (FIG. 5A) and a second configuration of the shape of the perforations (FIG. 5B), FIG. 6 a representation of a further example of a part of a cannula according to the invention in plan view and FIG. 7 a representation of a further example of an inventive cannula in the initial state in plan view (FIG. 7A) and in section along the section line I-I (FIG. 7B);

FIG. 1 shows schematically the connection of a so-called heart-lung machine or a so-called Mechanical Circulatory Support System (MCS) to ensure blood circulation in the entire human body, for example in the case of heart surgery or the like. The lung machine includes a so-called oxygenator 13, in which blood is enriched with oxygen. For this purpose, the patient's blood is diverted from the patient's venous system via a suitable supply hose system 15 and supplied to the oxygenator 13. From there, after oxygenation, it is fed back to the patient's arterial system via a pump 14 and a suitable discharge hose system 16. According to the invention, a cannula 1 inserted in the region of the femoral artery is used for this purpose and runs from the femoral artery via the aorta to the aortic arch. The cannula 1 is placed using the so-called Seldinger method. This means that no incision (surgical incision) is made in the femoral artery in the region of the entry of the cannula 1. By means of the cannula 1 according to the invention, oxygen-rich blood is brought from the oxygenator via the cannula directly into the region of the aortic arch in order to achieve a central perfusion of the body with oxygen-rich blood in the forward flow (flow from the aortic arch to the descending aorta). In contrast to a central cannulation, no sternotomy (longitudinal division of the sternum) or surgery on the open chest is necessary.

Figures 2A, 2B:
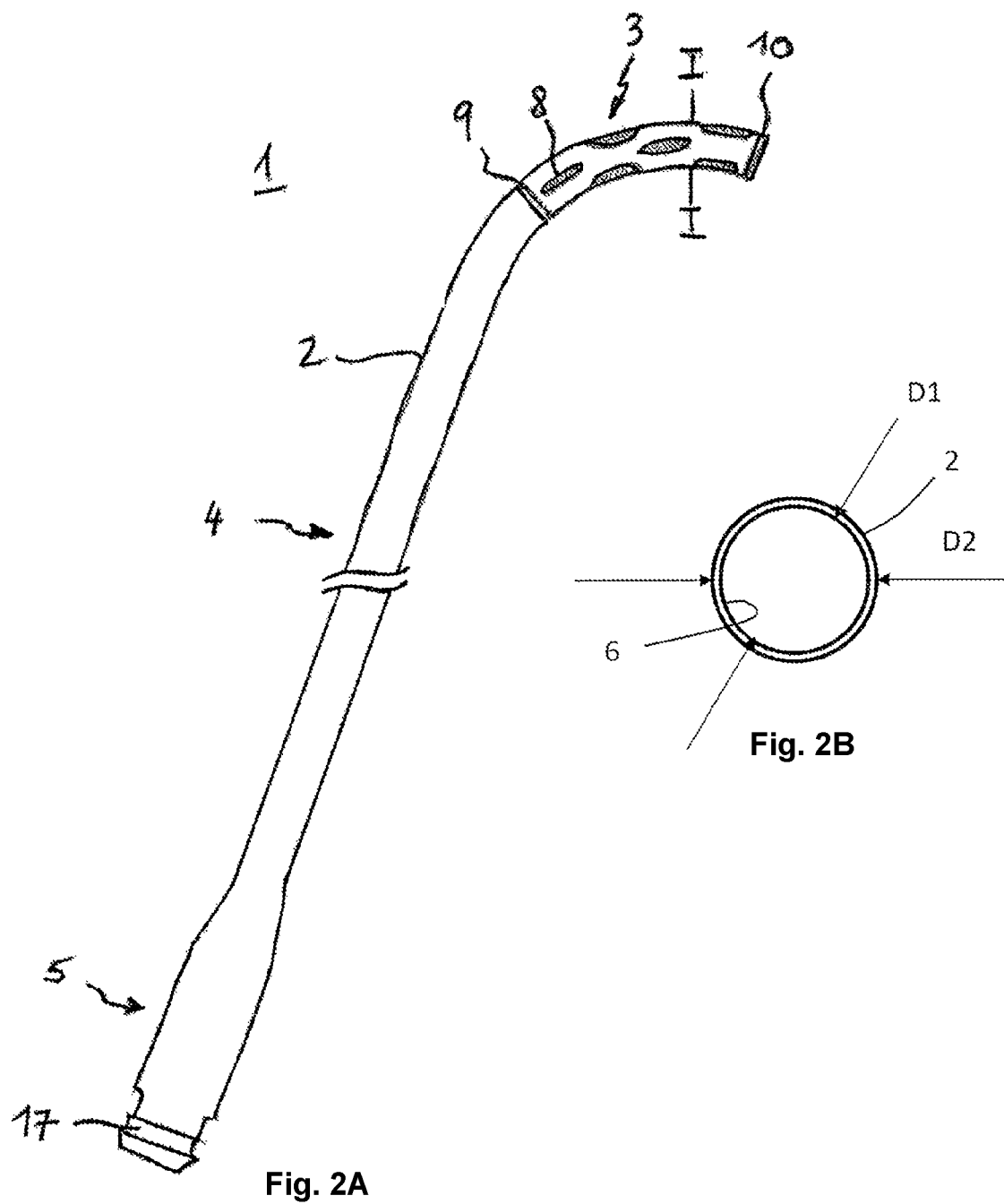
FIG. 2 is a representation of an example of a cannula according to the invention in the starting state in a top view (FIG. 2A) as well as in cross section along the section line I-I (FIG. 2B)

FIG. 2A shows a first embodiment of the cannula 1 according to the invention in a top view. The cannula 1 comprises a tubular body 2 with a front (distal) end region 3, a main region 4 and a lower, i.e. proximal, end region 5 with a connecting piece 17 which is used to connect the discharge hose system 16 of the oxygenator 13.

The tubular body 2 has (see FIG. 2B) a single lumen 6 which is circular and has a diameter D1. The tubular body 2 is also circular and has a diameter D2. The diameter D1 is in a range from 16 to 18 Fr. In the lower end region, the diameter of the lumen is 28 to 34 Fr.

The tubular body 2 can expediently have a constant diameter D1 and/or D2 in the main region 4 and/or in the front end region 3.

According to the invention, the tubular body 2 has a pre-curvature in the front end region. In the region of this pre-curvature, a plurality of perforations 8 are provided which are preferably positioned along the circumference of the tubular body 2, so that in the event of an unintentional closure of a perforation or of a portion of the perforations, for example due to vessel wall contact, the other perforations 8 remain clear. In the variant shown in FIG. 2A, the perforations 8 have an elongated preferred orientation which, for example, can be directed in the longitudinal direction of the cannula. In addition, the perforations can be arranged in a symmetrical arrangement with respect to one another along the circumference of the tubular body 2.

The distal end of the tubular body 2 is open.

The cannula 1 or its tubular body 2 are of sufficient length that the cannula 1 extends from the femoral artery up into the aortic arch. The cannula 1 or the tubular body 2 can accordingly have a length of approximately 40 to 60 cm.

The cannula 1 or the tubular body 2 can be coated with a material preventing blood clotting, for example in the form of a so-called heparin-containing coating. The tubular body 2 consists of plastic or a material based on plastic, which is flexible.

The front end region 3 of the tubular body is pre-curved in the initial state. The pre-curvature is flexible and designed such that it can be removed by means of an insertion aid (cf. FIG. 3A) by stretching the tubular body 2. The cannula 1 is kept ready for use in the form shown in FIG. 2A.

In the front end region 3, a contrast medium marker 9 is provided at the beginning of the region of the perforations 8 and at the distal end of the tubular body 2. The respective contrast medium marker 9, 10 serves for checking the position of the cannula or of the front end region 3 during insertion, i.e. indirectly via the position of the contrast medium markers 9, 10.

According to the invention, the cannula has no expandable or inflatable region in the front end region 3. In addition, perforations are only provided in the front end region 3, but not in the main region 4.

Figures 3A, 3B:
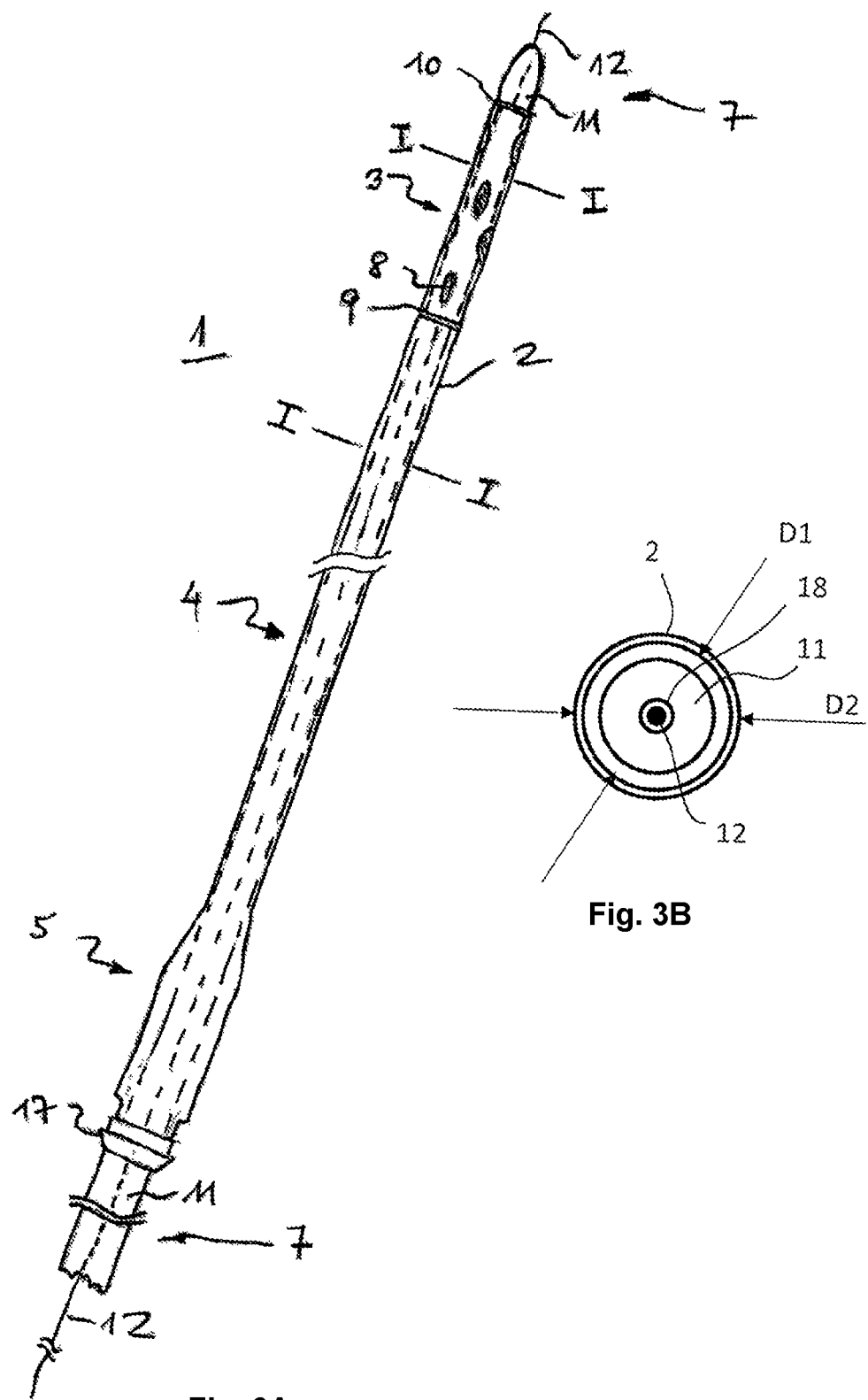
FIG. 3 shows the cannula according to FIG. 2 with inserted insertion aid in side view (FIG. 3A), in section along section line I-I (FIG. 3B) and in plan view with a partially withdrawn insertion aid (FIG. 3B), FIG. 4 the positioning of the front part of an embodiment of the cannula according to the invention after completion of the positioning, but still with an insertion aid.

An insertion aid 7 is provided for inserting the cannula by means of which the pre-curvature of the front end region 3 of the tubular body 2 can be eliminated, i.e. the tubular body 2 can be straightened. For this purpose, the insertion aid 7 comprises a mandrel 11, also called a straightener, which is arranged displaceably within the tubular body 2 and is rounded at its front distal end. The mandrel 11 is either led out centrally in the end region 5 on the connecting piece 17, as shown in FIG. 3A, or an additional branch (not shown in FIG. 3A) is provided for the mandrel 11. The mandrel 11 can expediently also be made of a plastic material which has a rigidity greater than the restoring force of the curvature in the upper region 3 of the tubular body 2.

In addition, the insertion aid 7 additionally comprises a flexible wire 12, which is used to slide in the mandrel 11 and the tubular body 2. The wire 12 runs, for example, in a guide channel 18 provided in the mandrel 11 which passes through the entire mandrel 11, so that the wire protrudes at the front of the distal end of the mandrel 11. When the cannula 1 is placed, the wire 12 is first inserted up to the aortic arch. Due to wall contact with the vessel wall when the cannula is pushed forward, the wire 12 bends in accordance with the course of the blood vessels. This defines the direction of insertion of the cannula 1 or of the mandrel 11.

As an alternative to the embodiment shown in FIG. 3A, the front region of the wire 12 can also have a curvature, for example by pretensioning it. The curvature may, for example, be small enough that it does not interfere with the tubular body 2 when withdrawn.

Due to the flexibility of the tubular body 2 and the mandrel 11, the cannula 1 equipped with the insertion aid 7 can be easily inserted into the aorta over the previously laid, i.e. inserted, wire 12 along the twisting courses of the femoral artery. The wire 12 is preferably a very tightly wound wire, preferably steel wire, which is extremely flexible due to its winding courses. The wire 12 can also be covered with a plastic tube (which is not shown in FIG. 3A) for better handling.

Figure 3C:
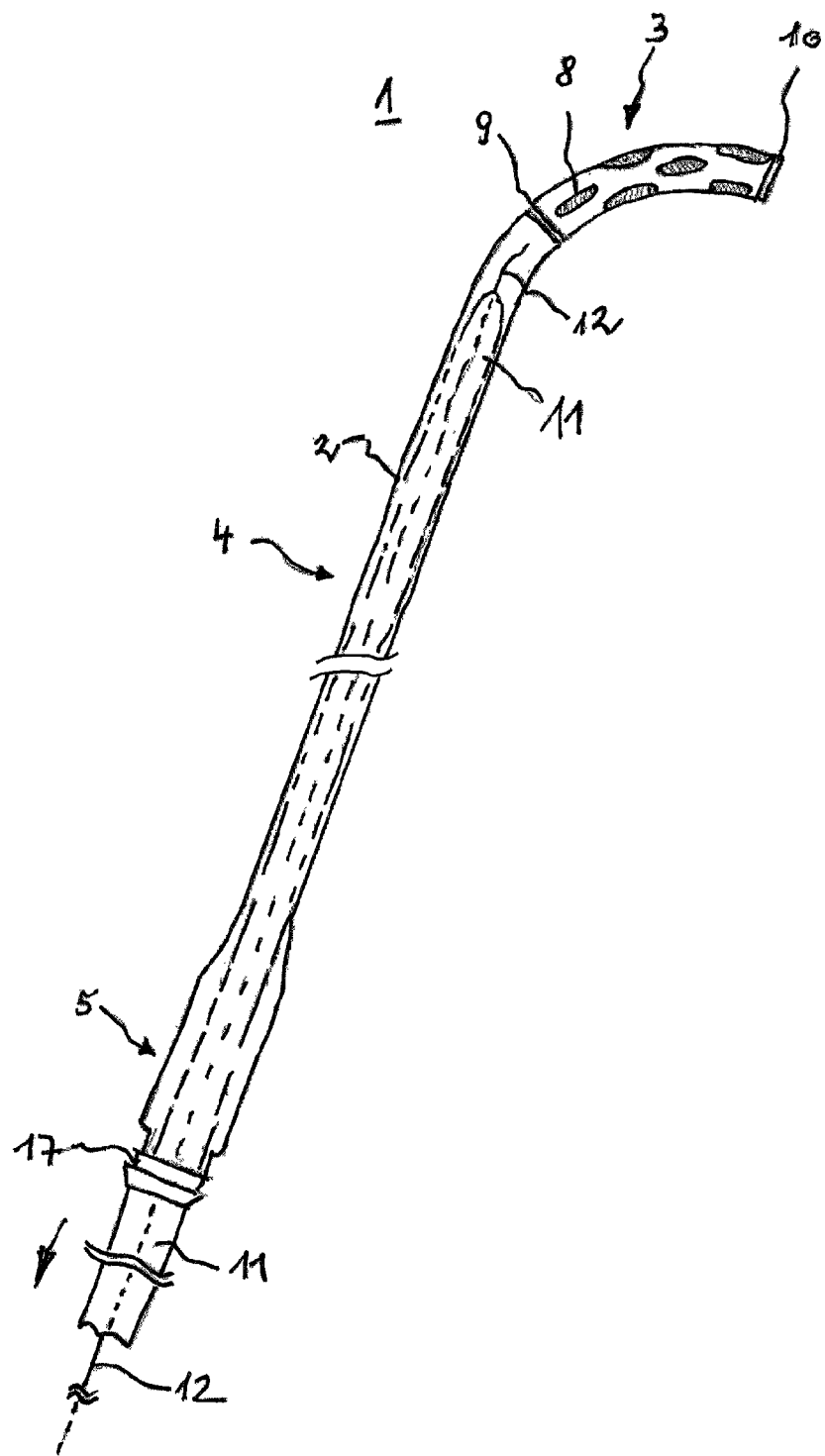

After the catheter 1 has been brought into position and the front end region 3 of the tubular body 2 is in the region of the aortic arch, the insertion aid 7 is carefully withdrawn from the cannula 1 while maintaining the position thereof, as shown in FIG. 3C. Here, as the proximal distance of the mandrel 11 increases, the front end region gradually curves back into its previously defined curvature. Subsequently, the mandrel 11 is withdrawn from the cannula 1 together with the wire 12, and the end region 5 is connected via the connecting piece 17 located there to the discharge hose system 16 of the oxygenator 13.

Figure 4:
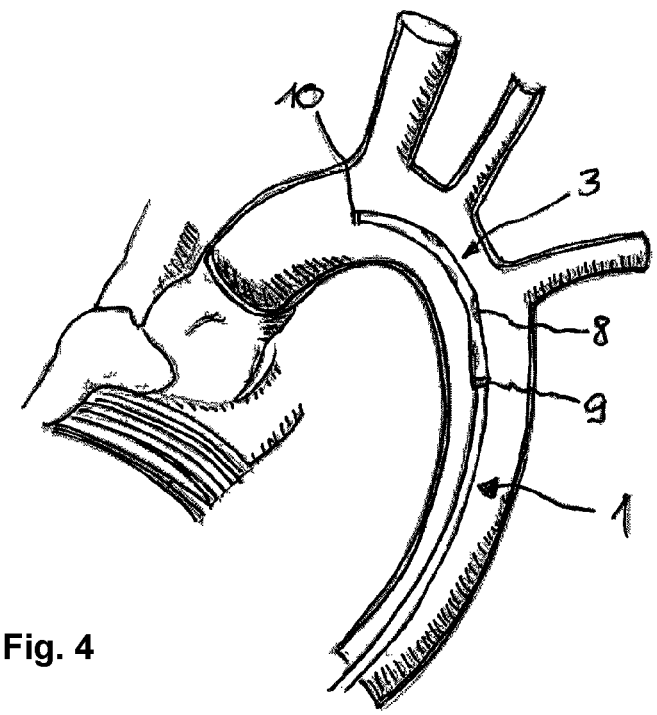

FIG. 4 shows the front end region 3 of the cannula in the correctly inserted state within the aortic arch. It is clear from the illustration that, due to the large number of perforations 8 provided in this region and the fact that the front end region 3 of the cannula cannot be expanded or inflated, oxygen-rich blood can reach all regions of the aortic arch as well as the cardiac outlet.

The perforations 8 are preferably arranged around the circumference of the front end region 3, that is to say not just on one side. Furthermore, they can be arranged in a specific arrangement pattern, preferably in a symmetrical arrangement pattern, around the circumference of the tubular body 2. In order to ensure an adequate supply of oxygen-rich blood at a relatively normal, i.e. not too high, pressure, at least 4, preferably at least 6, particularly preferably at least 8 perforations 8 are provided in the front region 3. For example, a total of 10 perforations can be provided.

According to expedient embodiments of the present invention shown in FIG. 5A and FIG. 5B, the perforations 8 are designed such that they have a hole width or a hole diameter D3 that increases, preferably continuously, from the inside to the outside of the tubular body 2, as shown in FIG. 5A and FIG. 5B. This has the advantage that there is no abrasive edge in the outer region of the respective perforation 8 by which deposits, such as plaque on the inside of the femoral artery or aorta, are inadvertently detached.

In the case of the hole configuration of the perforation 8 according to FIG. 5A, the inner wall of the hole shows a shape that is constantly expanding.

In the embodiment according to FIG. 5B, the perforations 8 on the outside of the tubular body 2 are rounded toward the inside, which also contributes to the aforementioned effect.

According to a further embodiment according to FIG. 6, the cannula according to the invention can preferably have a branch 19 in its rear end region 5 on which a tap 20 is provided. If necessary, the tap can be used for rinsing via a supply hose 21 and/or the system can be vented. Furthermore, the branch 19 or the tap 20 enables the system to be connected to a pressure measuring device (not shown in the drawings).

FIG. 7A shows a further useful embodiment of the cannula 22 according to the invention in which the front end region 3 of the tubular body 2 is divided into two sections. One section is provided with the pre-curvature and forms the curvature in the finished state of use, whereas the other section 23 of the front end region 3 is at least substantially straight. In the embodiment shown in FIG. 7A, the perforations 8 are located in the further section 23. Furthermore, in this embodiment, the curved region, i.e. the region of the pre-curvature, can be designed without perforation.

Otherwise, this configuration corresponds to the above-described configurations of the cannula 1 according to the invention with all their variations.

In summary, it can be stated that the present invention relates to a novel arterial cannula which enables an optimal supply of the aortic arch with oxygen-rich blood without a sternotomy or open chest surgery. This facilitates a very substantial relief for the patient. In addition, the treatment costs and regeneration costs are also significantly reduced compared to central cannulation. In addition, the cannula according to the invention can be produced in a simple and inexpensive manner.

LIST OF REFERENCE SIGNS 1 arterial cannula
2 tubular body
3 front end region
4 main region
5 rear end region
6 lumen
7 insertion aid
8 perforation
9 contrast medium marker
10 contrast medium marker
11 mandrel
12 wire
13 oxygenator
14 pump
15 supply hose system
16 discharge hose system
17 connecting piece
18 guide channel
19 branch
20 tap
21 supply hose
22 arterial cannula
23 straight portion

The invention claimed is:

1. An arterial cannula connectable to a heart-lung machine for supplying a human patient with oxygen-rich blood, comprising
a tubular body having a front end region for positioning in a region of the aortic arch of the patient, a main region, and a rear end region for connection to a supply side,
wherein the tubular body comprises a lumen,
wherein the tubular body is made of a flexible material,
wherein the length of the tubular body is dimensioned to facilitate placement of the cannula in a region of the femoral artery of the patient and extends into the region of the aortic arch,
wherein the tubular body provides a supply flow of oxygen-rich blood to the aortic arch,
and wherein perforations are provided in the front end region of the tubular body,
the front end region of the tubular body is at least partially pre-curved following the shape of the aortic arch,
an insertion aid located inside the tubular body for placing the cannula is slidable into the tubular body or withdrawn from the tubular body after the cannula has been placed,
wherein
the curvature of the front end region of the tubular body adjusts automatically after the cannula has been placed and the insertion aid is withdrawn, and
the tubular body has a single lumen.

2. The cannula according to claim 1, wherein perforations are provided exclusively in the front end region of the tubular body.

3. The cannula according to claim 1, wherein the lumen (6) is circular.

4. The cannula according to claim 1, wherein the lumen and/or the tubular body has/have a substantially constant diameter in a longitudinal direction of the cannula in the front end region and/or in the main region.

5. The cannula according to claim 1, wherein the front end region of the tubular body is inexpansive and/or uninflatable.

6. The cannula according to claim 1, comprising at least four of the perforations (8) are provided.

7. The cannula according to claim 1, wherein the perforations are arranged around the circumference of the tubular body.

8. The cannula according to claim 1, wherein the perforations have a shape with a preferred orientation, comprising a longitudinally extending and/or oval shape.

9. The cannula according to claim 8, wherein the preferred orientation of the shape of the perforations extends in the longitudinal direction of the tubular body.

10. The cannula according to claim 1, wherein the perforations have a hole diameter which gets larger, moving from inside to outside of the tubular body.

11. The cannula according to claim 1, wherein the perforations are rounded at an outer side of the tubular body.

12. The cannula according to claim 1, comprising contrast medium markers at the front end region of the tubular body.

13. The cannula according to claim 12, wherein the contrast medium markers determine a region of the perforations and/or a region of the curvature.

14. The cannula according to claim 12, wherein a contrast medium marker is positioned at a beginning of the region of the perforations and a contrast medium marker is positioned at an end of the region of the perforations or at an end of the tubular body.

15. The cannula according to claim 1, wherein the front end region of the cannula has at a distal end a substantially straight portion in which the perforations are exclusively located.

16. The cannula according to claim 1, wherein the insertion aid has a mandrel which is slidable into the tubular body and/or can be pushed through the tubular body.

17. The cannula according to claim 1, wherein the insertion aid comprises a wire.

18. The cannula according to claim 16, wherein the wire is guided in or on the mandrel.

\* \* \* \* \*